(12) United States Patent
Stiger

(10) Patent No.: US 6,679,860 B2
(45) Date of Patent: Jan. 20, 2004

(54) INTRALUMINAL THERAPY CATHETER WITH INFLATABLE HELICAL MEMBER AND METHODS OF USE

(75) Inventor: Mark L. Stiger, Santa Rosa, CA (US)

(73) Assignee: Medtronic Ave, Inc., Santa Rosa, CA (US)

( * ) Notice: Subject to any disclaimer, the term of this patent is extended or adjusted under 35 U.S.C. 154(b) by 156 days.

(21) Appl. No.: 09/885,072

(22) Filed: Jun. 19, 2001

(65) Prior Publication Data

US 2002/0193735 A1 Dec. 19, 2002

(51) Int. Cl.[7] .............................................. A61M 29/00

(52) U.S. Cl. ................................................ 604/101.01

(58) Field of Search ............................ 604/20, 96, 28; 606/194; 128/398.1; 600/3

(56) References Cited

U.S. PATENT DOCUMENTS

| | | | |
|---|---|---|---|
| 3,324,847 A | 6/1967 | Zoumboulis | |
| 3,438,375 A | 4/1969 | Ericson | |
| 4,404,971 A | 9/1983 | LeVeen et al. | |
| 4,445,892 A | 5/1984 | Hussein et al. | |
| 4,696,668 A | 9/1987 | Wilcox | |
| 4,762,130 A | * 8/1988 | Fogarty et al. | 128/348.1 |
| 4,781,677 A | 11/1988 | Wilcox | |
| 5,002,532 A | 3/1991 | Gaiser et al. | |
| 5,071,406 A | 12/1991 | Jang | |
| 5,181,911 A | 1/1993 | Shturman | |
| 5,199,939 A | 4/1993 | Dake et al. | |
| 5,226,888 A | 7/1993 | Arney | |
| 5,226,889 A | 7/1993 | Sheiban | |
| 5,261,878 A | 11/1993 | Galindo | |
| 5,269,757 A | 12/1993 | Fagan et al. | |
| 5,295,959 A | 3/1994 | Gurbel et al. | |
| 5,308,356 A | * 5/1994 | Blackshear, Jr. et al. | 606/194 |
| 5,320,605 A | 6/1994 | Sahota | |
| 5,370,608 A | * 12/1994 | Sahota et al. | 604/20 |
| 5,411,466 A | 5/1995 | Hess | |
| 5,413,557 A | 5/1995 | Solar | |
| 5,415,634 A | 5/1995 | Glynn et al. | |
| 5,484,411 A | 1/1996 | Inderbitzen et al. | |
| 5,484,412 A | 1/1996 | Pierpont | |
| 5,540,659 A | 7/1996 | Teirstein | |
| 5,554,119 A | 9/1996 | Harrison et al. | |
| 5,556,389 A | 9/1996 | Liprie | |
| 5,616,114 A | 4/1997 | Thornton et al. | |
| 5,618,266 A | 4/1997 | Liprie | |

(List continued on next page.)

FOREIGN PATENT DOCUMENTS

| | | |
|---|---|---|
| EP | 0 593 136 B1 | 3/1997 |
| EP | 0 810 004 A2 | 12/1997 |
| EP | 0 972 535 A2 | 1/2000 |
| WO | WO 98/02096 A1 | 1/1998 |
| WO | WO 00/27454 A1 | 5/2000 |

*Primary Examiner*—Henry Bennett
*Assistant Examiner*—Sabrina Dagostino
(74) *Attorney, Agent, or Firm*—Ingrassia Fisher & Lorenz, P.C.

(57) ABSTRACT

The invention is an intraluminal therapy catheter having a least two treatment members disposed near the distal end of the catheter, the members being independently inflatable to perform angioplasty and/or fluid-sourced brachytherapy. A first treatment member is helically mounted about the shaft of the catheter, and forms a helical perfusion channel when inflated into contact with the vessel being treated. In a first embodiment of the invention, the second treatment member is also helically mounted about the catheter shaft and capable of forming a helical perfusion channel when inflated into contact with the vessel. The first and second treatment members are intertwined to form a double helix configuration wherein each member is capable of being inflated to generally fill the helical perfusion channel created by simultaneous inflation of the other member. In a second embodiment of the invention, the second treatment member is a tubular balloon mounted generally coaxially about the catheter shaft, adjacent to the first treatment member.

11 Claims, 5 Drawing Sheets

U.S. PATENT DOCUMENTS

| | | |
|---|---|---|
| 5,632,760 A | 5/1997 | Sheiban et al. |
| 5,634,928 A | 6/1997 | Fischell et al. |
| 5,639,274 A | 6/1997 | Fischell et al. |
| 5,643,171 A | 7/1997 | Bradshaw et al. |
| 5,653,683 A | 8/1997 | D'Andrea |
| 5,662,580 A | 9/1997 | Bradshaw et al. |
| 5,725,535 A | 3/1998 | Hegde et al. |
| 5,733,299 A | 3/1998 | Sheiban et al. |
| 5,735,816 A | 4/1998 | Lieber et al. |
| 5,749,852 A | 5/1998 | Schwab et al. |
| 5,782,740 A | 7/1998 | Schneiderman |
| 5,782,742 A | 7/1998 | Crocker et al. |
| 5,840,064 A | 11/1998 | Liprie |
| 5,846,246 A | 12/1998 | Dirks et al. |
| 5,851,171 A | 12/1998 | Gasson |
| 5,882,290 A | 3/1999 | Kume |
| 5,891,091 A | 4/1999 | Teirstein |
| 5,910,101 A | 6/1999 | Andrews et al. |
| 5,938,582 A | 8/1999 | Ciamacco, Jr. et al. |
| 5,947,924 A | 9/1999 | Liprie |
| 5,951,458 A | 9/1999 | Hastings et al. |
| 5,971,955 A | 10/1999 | Nap et al. |
| 5,976,106 A | 11/1999 | Verin et al. |
| 6,033,357 A | 3/2000 | Ciezki et al. |
| 6,048,299 A | 4/2000 | Hoffmann |
| 6,059,713 A | 5/2000 | Urick et al. |
| 6,059,812 A | 5/2000 | Clerc et al. |
| 6,068,611 A | 5/2000 | Loffler et al. |
| 6,074,338 A | 6/2000 | Popowski et al. |
| 6,074,339 A | 6/2000 | Gambale et al. |
| 6,077,213 A | 6/2000 | Ciezki et al. |
| 6,093,142 A | 7/2000 | Ciamacco, Jr. |
| 6,099,454 A | 8/2000 | Hastings et al. |
| 6,099,499 A | 8/2000 | Ciamacco, Jr. |
| 6,110,097 A | 8/2000 | Hastings et al. |
| 6,117,065 A | 9/2000 | Hastings et al. |
| 6,117,386 A | 9/2000 | Stiger |
| 6,142,926 A | 11/2000 | Schneiderman |
| 6,149,574 A | 11/2000 | Trauthen et al. |
| 6,156,053 A | 12/2000 | Gandhi et al. |
| 6,159,140 A | 12/2000 | Loeffler et al. |
| 6,176,821 B1 | 1/2001 | Crocker et al. |
| 6,190,536 B1 | 2/2001 | Lokhandwala et al. |
| 6,196,963 B1 | 3/2001 | Williams |

\* cited by examiner

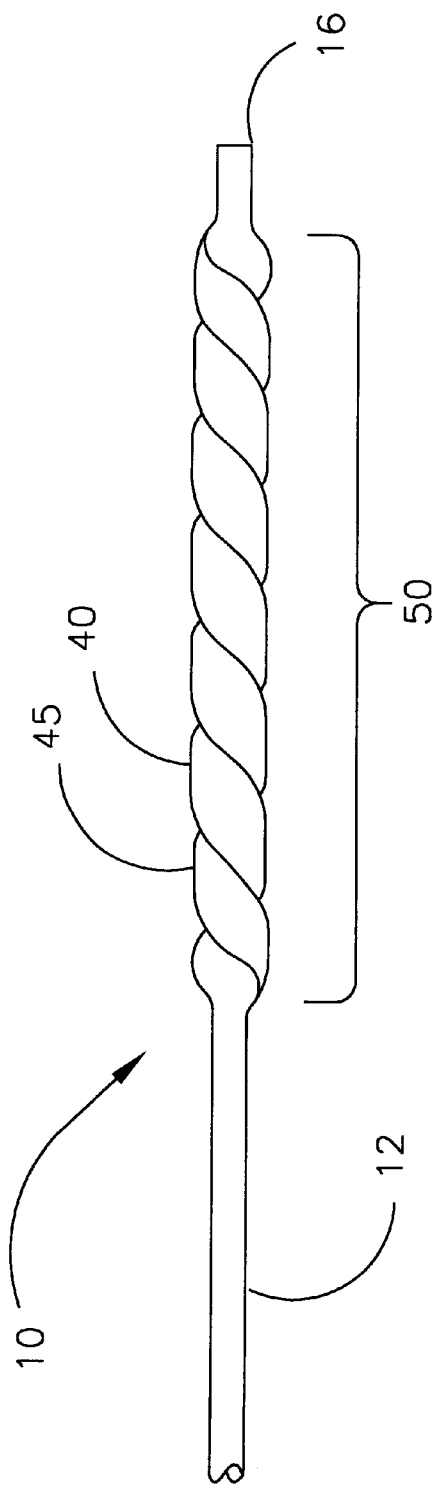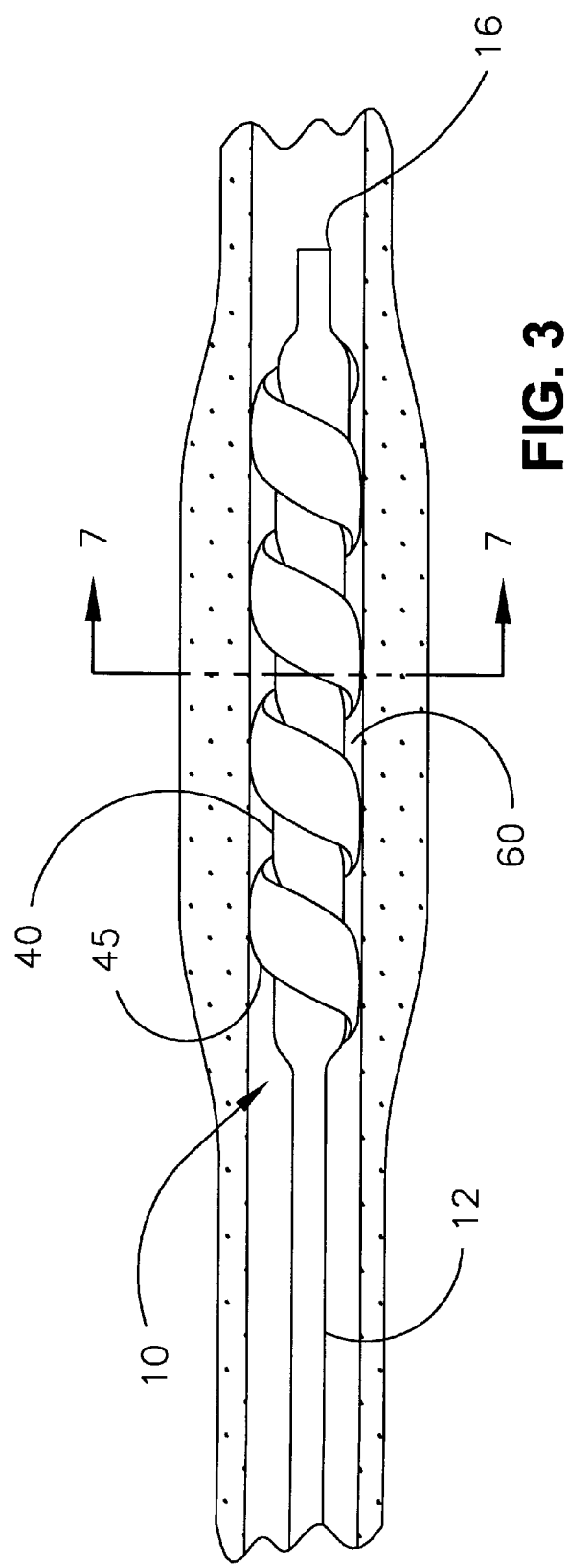

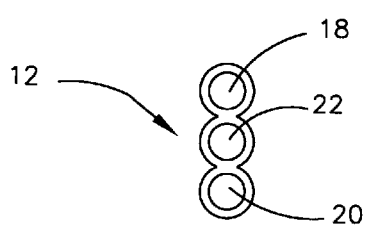
FIG. 4
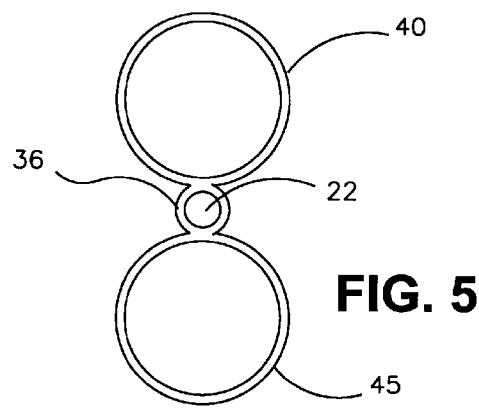
FIG. 5
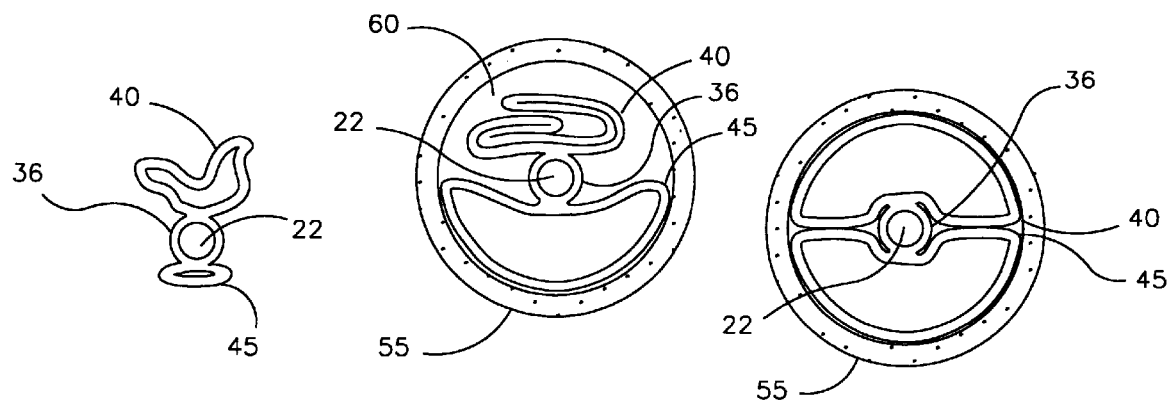
FIG. 6  FIG. 7  FIG. 8
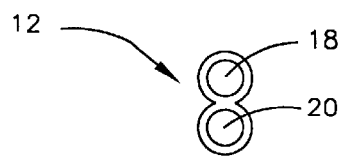
FIG. 9
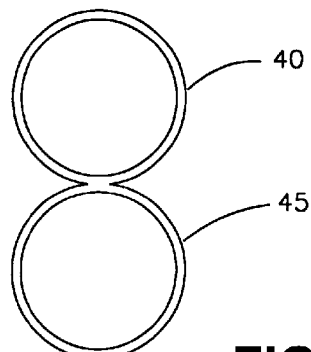
FIG. 10

INTRALUMINAL THERAPY CATHETER WITH INFLATABLE HELICAL MEMBER AND METHODS OF USE

FIELD OF THE INVENTION

The present invention relates to intraluminal therapy devices and more particularly to catheters intended for use in angioplasty and brachytherapy.

BACKGROUND OF THE INVENTION

Stenosis is a narrowing or constriction of a duct or canal. A variety of disease processes, such as atherosclerotic lesions, immunological reactions, congenital abnormalities and the like, can lead to stenoses of arteries or other vessels. Stenosis of a coronary artery can reduce blood flow sufficiently to cause myocardial ischemia. Percutaneous transluminal coronary angioplasty (PTCA), the insertion and inflation of a balloon catheter in a coronary artery to affect its repair, is widely accepted as an option in the treatment of obstructive coronary artery disease. In general, PTCA is used to increase the lumen diameter of a coronary artery that is partially or totally obstructed by a build-up of cholesterol fats or atherosclerotic plaque. In PTCA, a coronary guiding catheter provides a channel from outside the patient to the ostium of a coronary artery. A balloon catheter is advanced over a small diameter, steerable guidewire through the guiding catheter, into the artery, and across the stenosis. The tubular balloon near the tip of the catheter is inflated to expand the narrowing. Dilation of the occlusion, however, can form flaps, fissures and dissections which threaten abrupt reclosure of the dilated vessel or even perforations in the vessel wall. To treat or prevent such sequelae, tubular stents are often placed within the angioplasty site to scaffold the vessel lumen. Since a tubular balloon typically occludes, or shuts off blood flow through an artery, angioplasty can be conducted for only short periods before the lack of blood flow may cause ischaemia or tissue damage. To solve this problem, some PTCA catheters include a bypass, or perfusion channel, so that blood continues to flow through the artery during dilatation.

In some devices, the perfusion channel is a hollow shaft extending through the balloon. Blood ingress to and egress from the hollow shaft is provided by open ports in the shaft, located proximal and distal to the balloon. In other PTCA catheters, a helical balloon mounted around the catheter shaft forms a spiral perfusion channel between the wall of the vessel and the inflated balloon. The flow rate of blood passing through the spiral channel depends upon the channel cross sectional area, which is related, in part, to the channel width between adjacent turns of the helical balloon. However, widening the channel width to increase flow also decreases the surface area of the stenosis that is exposed to the dilating force of the helical balloon. Thus, there are design trade-offs that attend dilatation balloon catheters having spiral perfusion channels. In other prior art perfusion angioplasty catheters, the catheter shaft is mounted off-center within a coiled balloon such that blood can flow through the center of the coil.

Other intraluminal therapies include atherectomy (mechanical removal of plaque residing inside an artery), laser ablative therapy and the like. While the stenosis or occlusion is greatly reduced using these therapies, many patients experience a recurrence of the stenosis over a relatively short period. Restenosis, defined angiographically, is the recurrence of a 50% or greater narrowing of a luminal diameter at the site of a prior therapy. Additionally, researchers have found that angioplasty or placement of a stent in the area of the stenosis can irritate the blood vessel and cause rapid reproduction of the cells in the medial layer of the blood vessel, developing restenosis through a mechanism called medial hyperplasia. Restenosis is a major problem which limits the long-term efficacy of invasive coronary disease therapies. Additionally, the rapid onset of restenosis is compounded by the lack of ability to predict which patients, vessels, or lesions will undergo restenosis.

Although the mechanism of restenosis is not fully understood, clinical evidence suggests that restenosis results from a migration and rapid proliferation of a subset of predominately medially derived smooth muscle cells, which is apparently induced by the injury from the invasive therapy. Such injury, for example, is caused by the angioplasty procedure when the balloon catheter is inflated and exerts pressure against the artery wall, resulting in medial tearing. It is known that smooth muscle cells proliferate in response to mechanical stretching and the resulting stimulation by a variety of growth factors. Also, intimal hyperplasia can contribute to restenosis, stimulated by the controlled therapeutic injury. It is believed that such proliferation stops one to two months after the initial invasive therapy, but that these cells continue to express an extracellular matrix of collagen, elastin and proteoglycans. Additionally, animal studies have shown that during balloon injury, denudation of endothelial cells can occur, followed by platelet adhesion and aggregation, and the release of platelet-derived growth factor (PDGF) as well as other growth factors. As mentioned above, this mass of tissue can contribute to the re-narrowing of the vascular lumen in patients who have restenosis. It is believed that a variety of biologic factors are involved in restenosis, such as the extent of the tissue injury, platelets, inflammatory cells, growth factors, cytokines, endothelial cells, smooth muscle cells, and extracellular matrix production, to name a few.

It has been found that irradiating the blood vessel walls at the treatment site can reduce or prevent hyperplasia. Precise control over the amount of radiation is important, since insufficient radiation will not prevent restenosis and excessive radiation can further damage the blood vessel or surrounding tissues. To prevent unnecessary radiation beyond the site of the stenosis, it is preferable to introduce a small radiation source into the treated vessel. The prior art contains numerous examples of brachytherapy catheters and radiation sources for this purpose. One type of known devices is a catheter that delivers to the treatment site a linear radioactive filament, or radioactive guidewire source.

Another known prior art device is a catheter having a spherical inflatable chamber adjacent the catheter distal end. A fluid containing a radioactive material is pumped into the chamber, inflating the chamber and treating the vessel walls with ionizing radiation. The chamber can be inflated against the vessel wall, displacing any blood that may attenuate irradiation of the tissue by the radiation fluid source within the chamber. Irradiating a segment of an artery or the like generally takes from about 3 to 45 minutes. As happens in angioplasty, however, inflating the chamber against the vessel wall will stop blood flow, so it can be inflated only for a short time. There are known brachytherapy catheters that include a perfusion channel formed through the center of a stack of toroidal elements that can be inflated with radiation fluid. The complexity of making such a device, and its requirement for a cumbersome sheath to envelope the inflation element during its placement in the vessel are significant disadvantages.

Furthermore, in all prior art perfusion angioplasty catheters, the perfusion feature is built-in, such that the clinician needs to pre-select such a catheter before beginning the treatment procedure. Therefore, any design trade-offs, such as greater deflated profile or complicated structure, must be accepted and planned for, or else a catheter exchange is required. What is needed is a device that is capable of state-of-the-art angioplasty or brachytherapy with perfusion that is selectively available during the procedure, should the need arise.

The use of prior art angioplasty and brachytherapy catheters in the same patient has typically required exchanging one type of device for the other, which can be tedious and time-consuming. Thus, it is an object of the invention to provide a single device that is capable of performing both angioplasty and brachytherapy.

A further object of the invention is to provide a device that is capable of performing angioplasty and brachytherapy simultaneously.

Another object of the invention is to provide an intraluminal therapy catheter that is capable of selectively forming a perfusion channel during treatment.

SUMMARY OF THE INVENTION

The present invention is an intraluminal therapy catheter having at least two inflatable treatment members disposed near the distal end of the catheter. A first treatment member is helically mounted about the shaft of the catheter and forms a helical perfusion channel when inflated into contact with the vessel being treated.

In a first embodiment of the invention, the second treatment member is also helically mounted about the catheter shaft and is also capable of forming a helical perfusion channel when inflated into contact with the vessel. The first and second treatment members are intertwined to form a double helix configuration wherein each member is capable of being inflated to generally fill the helical perfusion channel created by simultaneous inflation of the other member. In this embodiment, simultaneous inflation of both treatment members forms a generally cylindrical treatment body. Either treatment member can be selectively deflated to leave a helical perfusion channel formed by the other, still inflated, treatment member. Both treatment members are deflated to a low profile configuration during insertion and withdrawal of the catheter from the patient.

The first embodiment of the invention has several useful modes of operation. In a first mode, simultaneous inflation of both treatment members provides generally cylindrical dilation of a diseased blood vessel, comparable to PTCA with a single tubular balloon. Advantageously, in a second mode of operation, if the patient experiences discomfort due to ischaemia, a first helical treatment member can be deflated to form a perfusion channel, while the second treatment member remains inflated to continue dilation of the vessel, albeit in a helical pattern. Blood flowing through the perfusion channel can alleviate the patient's discomfort, as described above. If so desired, the first helical treatment member can be re-inflated while the second helical treatment member is deflated, such that no part of the vessel wall is untreated, and distal perfusion can be provided throughout the procedure.

In a third mode of operation of the first embodiment, the treatment members are simultaneously inflated with radioactive fluid to provide brachytherapy to the treatment area, as may be desired following a procedure such as PTCA. In a fourth mode of operation, comparable to the second mode described above, the treatment members may be deflated individually, and/or alternatively to provide complete brachytherapy treatment while alleviating ischaemia, as necessary.

In a fifth mode of operation of the first embodiment, the first treatment member is inflated to dilate the diseased vessel and the second treatment member is inflated with radioactive fluid simultaneously with, or immediately following the dilation provided by the first treatment member.

In a second embodiment of the invention, the second treatment member is a tubular balloon mounted generally coaxially about the catheter shaft, adjacent to the first treatment member. Using this structure, the second treatment member can perform angioplasty and the first treatment member can perform brachytherapy immediately afterwards, without having to make a catheter exchange. After the PTCA balloon is deflated, the catheter is moved sufficiently to position the first treatment member within the dilated portion of the vessel, then the first treatment member is inflated with radioactive fluid.

In all of the embodiments and modes of operation described above, if dilation is the intended function, then the treatment member is fabricated from inelastic polymeric material, comparable to PTCA balloons. If brachytherapy is intended, then optionally, the treatment member can be fabricated from elastic material.

BRIEF DESCRIPTION OF THE DRAWINGS

These and other features, aspects and advantages of the present invention will become better understood with reference to the following description, appended claims, and accompanying drawings where:

FIG. 2 is an elevational view of a distal portion of a catheter in accordance with the first embodiment of the invention, wherein both inflatable treatment members are shown in deflated condition;

FIG. 3 is an elevational view of a distal portion of a catheter in accordance with the first embodiment of the invention, the catheter is shown deployed within a longitudinally sectioned portion of a stenotic vessel, one treatment member is inflated and the other treatment member is deflated;

FIG. 4 is a transverse sectional view of a first multi-lumen tubing useable in fabricating an embodiment of the invention;

FIG. 5 is a transverse sectional view of a treatment portion in a first embodiment of the invention, two of the treatment members are shown inflated;

FIG. 6 is a transverse sectional view of the treatment portion in the first embodiment of the invention, two of the treatment members are shown deflated;

FIG. 7 is a transverse sectional view taken along line 7—7 in FIG. 3, showing the treatment portion of the first embodiment of the invention within a vessel being treated;

FIG. 8 is a transverse sectional view similar to FIG. 7, except that both of the treatment members are shown inflated;

FIG. 9 is a transverse sectional view of a second multi-lumen tubing useable in fabricating another version of the first embodiment of the invention;

FIG. 10 is a transverse sectional view of the treatment portion in the other version of the first embodiment of the invention, two of the treatment members are shown inflated;

DETAILED DESCRIPTION OF THE INVENTION

Figure 1:
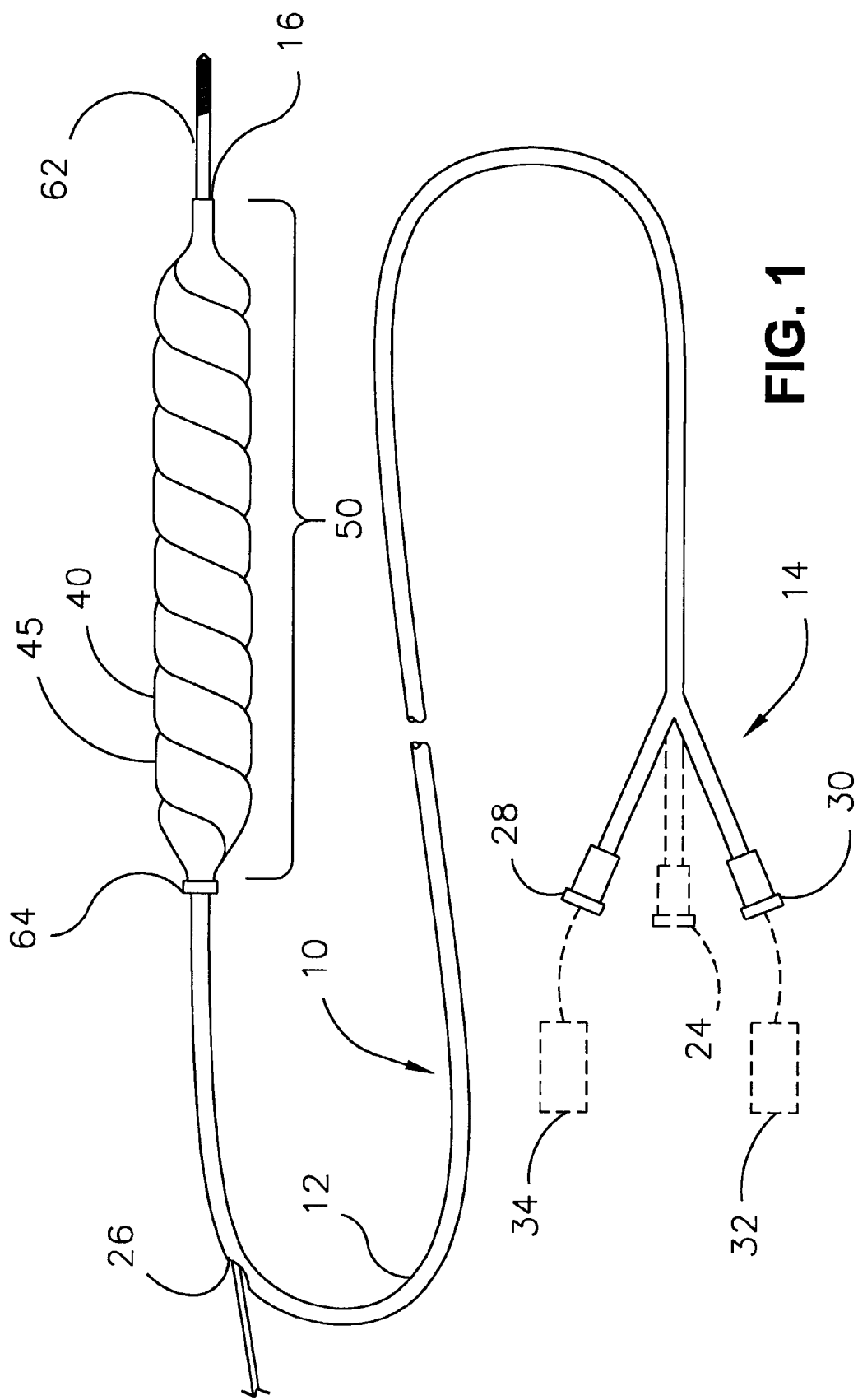
FIG. 1 is a fragmented illustration of a catheter in accordance with a first embodiment of the invention.

An apparatus is provided by the present invention that allows for angioplasty, intraluminal radiation therapy (also called brachytherapy), or a combination of the two treatments. The invention is a catheter including a pair of inflatable treatment members disposed near the distal end of the catheter. FIG. 1 shows a first embodiment of the invention in which catheter 10 includes flexible elongate body 12 having proximal and distal ends 14, 16. Lumens 18, 20 (see FIGS. 4 and 9) extend from proximal end 14 to blind ends near distal end 16. Optionally, guidewire lumen 22 also extends through body 12 from distal end 16 to either proximal fitting 24, shown in alternate form, or to guidewire port 26, which is located proximal of distal end 16, but substantially distal to proximal end 14. Fittings 28, 30 are affixed to proximal end 16, in communication with lumens 18, 20, and are connected, during use, with fluid sources 32, 34, shown schematically. Optionally, lumens 18, 20 may be connected to a single fluid source until and unless separate inflation of helical members 40, 45 is desired. Fluid sources 32, 34 may be specialized for pressurizing fluid during angioplasty, or for injecting fluid containing radioactive isotopes for brachytherapy, as will be understood by those of skill in the art.

Adjacent distal end 16, helical treatment members 40, 45 are disposed in parallel double-helix configuration 50 and are in fluid communication with lumens 18, 20, respectively. Catheter body 12 may be formed from a multi-lumen extrusion, as shown in FIGS. 4 and 9. Optionally, single-lumen tubes can be extruded separately, then joined side-by-side to form multi-lumen tubing using a suitable adhesive, solvent bonding or heat bonding techniques. One or both helical members 40, 45 may be formed of thermoplastic elastomer (TPE) or other high strength, thermoplastic polymer, such as those used to blow-mold dilatation balloons. Typical of such polymers are polyolefins, polyamides, polyethylene terephthalate (PET), TPE's such as PELLETHANE®, a polytetramethylene glycol based polyurethane elastomer from Dow Plastics, Midland, Mich., USA., and block copolymers such as PEBAX®, a polyether block amide from Elf Atochem North America, Inc., Philadelphia, Pa., U.S.A. When using such materials, multi-lumen tubing can be twisted, then blow molded, as shown in cross-section in FIGS. 5 and 10, into double helix configuration 50. Alternatively, single-lumen tubes can be separately blow molded into helical members 40, 45, which are then joined into double helix configuration 50 using a suitable adhesive, solvent bonding or heat bonding techniques. Double helix configuration 50 may be formed as part of elongate body 12, or it may be formed separately, then joined to the remainder of elongate body 12, which can comprise a multi-lumen extrusion.

Alternatively, one or both helical treatment members 40, 45 may be formed of an elastic material, which would not require blow molding. In this embodiment, elastic tubing, typically formed of silicone or latex material, is wrapped around central shaft 36, which may enclose guidewire lumen 22, thus forming double helix configuration 50. As shown in FIG. 6, helical member 45 is formed of elastic material, and helical member 40 is formed of inelastic material. When deflated, inelastic helical member 40 collapses loosely, forming wrinkles and/or wings, as shown in the partially deflated configuration of member 40 in FIG. 7. In this combination, helical member 45 collapses elastically when deflated, shrinking down to a smaller profile than the profile created by deflating inelastic helical member 40. The advantage of this combination is that the perfusion channel created by deflating elastic member 45 has a larger cross-section than the perfusion channel created by deflating inelastic member 40, thus providing greater blood flow.

In FIG. 1, both helical treatment members 40,45 are shown inflated. If helical members 40, 45 are both formed of a high strength, thermoplastic material, then simultaneous inflation thereof forms a generally cylindrical treatment body that is capable of performing cylindrical dilatation of vessels. If helical members 40,45 are both formed of an elastic material, then simultaneous inflation thereof with radioactive fluid forms a generally cylindrical configuration that is capable of performing brachytherapy. Helical members formed of high strength, thermoplastic material can also be inflated with radioactive fluid to perform brachytherapy. However, it is not advisable to use such a hazardous fluid to inflate any members to dilatation pressures, as leakage may occur, resulting in a potentially dangerous injection of radioactive fluid into the patient's system.

FIG. 2 shows the first embodiment of the invention, with both helical members 40, 45 deflated into a configuration suitable for insertion and/or withdrawal from a patient's vessels. FIG. 3 shows catheter 10 according to the first embodiment of the invention, performing therapy in stenotic vessel 55. In this view, helical member 45 is inflated against vessel 55, and helical member 40 is deflated to form helical perfusion channel 60. Since the treatment (either dilatation or brachytherapy) provided by member 45 is limited to a helical pattern, it may be desirable to reverse the inflation status of members 40, 45 such that helical member 40 is inflated to provide treatment and helical member 45 is deflated to provide a perfusion channel. It may also be advantageous to periodically alternate the inflation status of members 40, 45, to ensure therapy of the entire stenosis in vessel 55, while providing continuous perfusion across the region being treated.

FIG. 7 is a transverse sectional view taken along line 7—7 in FIG. 3, showing the treatment portion of the first embodiment of the invention within stenotic vessel 55. Helical member 45 is shown inflated into contact with the wall of vessel 55 for angioplasty or brachytherapy thereof, and helical member 40 is shown deflated, creating perfusion channel 60. FIG. 8 shows a transverse sectional view that is similar to FIG. 7, except that both helical members 40, 45 are inflated into contact with vessel 55 for treatment thereof.

Figure 11:
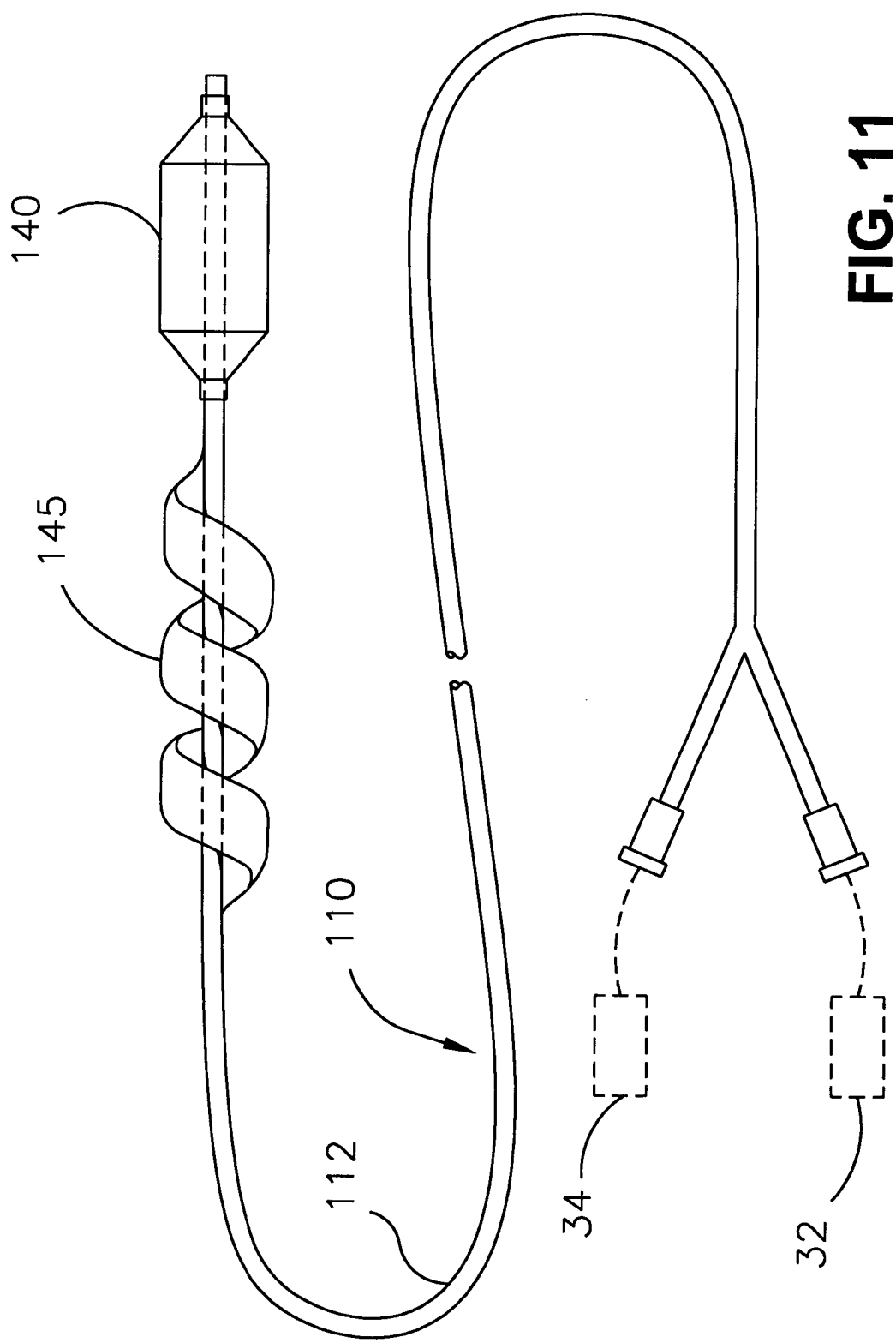
FIG. 11 is a fragmented illustration of a catheter in accordance with a second embodiment of the invention.

FIG. 11 shows a second embodiment of a medical device in accordance with the invention, wherein catheter 110 includes elongate body 112, dilatation balloon 140, and helical treatment member 145. The structural elements of catheter 110 are similar to the elements of catheter 10, however, helical member 145 is located proximal to balloon 140 instead of these two elements being coaxially arranged. For example, balloon 140 and helical member 145 are in fluid communication with lumens 18, 20 (see FIGS. 4 and 9). Catheter 110 permits intravascular radiotherapy immediately following PTCA, without having to exchange catheters. After performing angioplasty with balloon 140, catheter 110 is moved to locate helical member 145 within the dilated area of the vessel, and helical member 145 is inflated with radioactive fluid to perform brachytherapy. Optionally, treatment member 145 can be located distal to balloon 140.

A catheter according to the present invention is preferably provided with a conventional "rapid exchange" or "single operator exchange" feature. In general, exchanging catheters having full-length lumens over exchange-length guidewires is difficult because such procedures require at least two operators who must be in communication during the procedure, requiring more time and increasing the likelihood of contamination by dropping the guidewire from the sterile field, for example. Thus, rapid exchange catheters include a short guidewire lumen that enables a single operator to anchor or hold a standard-length guidewire when the catheter is removed from the body with the exchange occurring over the short guidewire portion that extends from the patient.

In the rapid-exchange embodiment shown in FIG. 1, guidewire port 26 is typically located at such a point along the length of the catheter so as to limit the guidewire length necessary to position a treatment portion of the catheter in close proximity to an in vivo treatment site, such as about 20 cm from distal end 16 of catheter 10. Guidewire 62 can enter distal end 16, pass through guidewire lumen 22, and exit from port 26. Furthermore, in the rapid exchange embodiment, the portion of body 12 proximal to port 26 can lack guidewire lumen 22, since the guidewire does not extend through this portion of catheter 10. Alternatively, a conventional over-the-wire configuration may also be included wherein the guidewire lumen 22 runs substantially the entire length of catheter 10, and wherein port 26 would be located in fitting 24. It is to be understood that, since rapid exchange catheters utilize guidewires, these devices are considered to be a subset of over-the-wire catheters.

Radiopaque marker 64 is preferably provided and can be attached at one or more locations along catheter body 12. Preferably, at least one location of radiopaque marker 64 is adjacent the proximal ends of helical treatment members 40,45. In FIG. 11, marker 64 (not shown) may be about, within, or adjacent the proximal neck of balloon 140. Radiopaque marker 64 is used to provide a fluoroscopic indication of the location of treatment members 40, 45, 140, and 145, thus allowing the operator to adjust the position of the treatment members in proximity to the in vivo site targeted for therapy. Radiopaque markers are commonly made from metals having high X-ray attenuation coefficients, such as gold or platinum, or alloys thereof.

In the present invention, catheters 10, 110 are preferably formed from any materials that are biocompatible, are biostable, and minimize irritation to the body passageway during treatment. Such materials may include a polymer, a metal, or combinations thereof. Biocompatible and biostable polymers are those which stimulate a relatively low chronic tissue response. Preferably, polymer materials used are radiolucent and may also be optically transparent. Suitable polymers can be selected from the group comprising a polyurethane, a silicone, a polyester, a polyolefin, a block copolymer and other thermoplastic or thermoset plastic materials known to be suitable for construction of medical devices. Although catheters 10, 110 can incorporate metals such as stainless steel or shape memory alloys such as nitinol, these materials should be avoided when forming at least treatment regions of bodies 12, 112 respectively, where the metal could block the intended emission of radiation.

The diameter of guidewire lumen 22 typically measures about 0.41 mm (0.016 inch) for guidewires having a diameter of about 0.36 mm (0.014 inch), depending upon the intended clinical application for catheters 10, 110. For example, smaller diameters may be used in neurovascular applications, while larger diameters may be used in peripheral artery applications.

Figure 12:
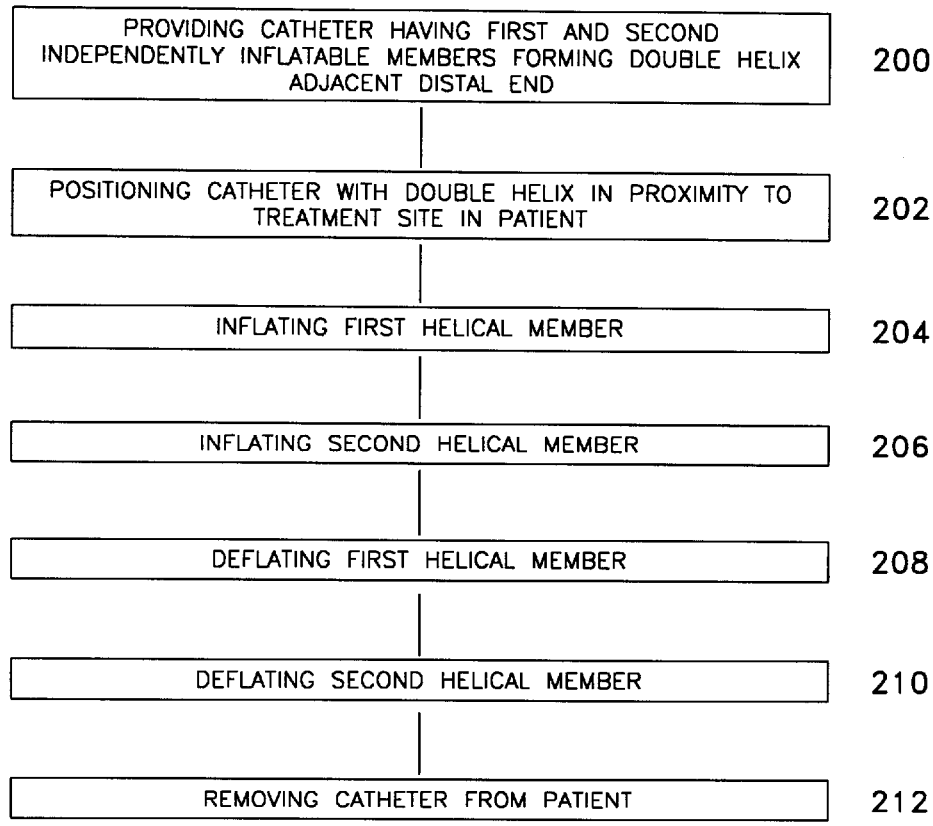
FIG. 12 is a flow chart depicting a method of using a catheter of the present invention.

According to a method of using the invention, as shown in FIG. 12, catheter 10 is percutaneously inserted into the patient's vessels, preferably traversing a vein or artery until helical treatment members 40, 45 of catheter 10 reach the desired site for therapy (steps 200, 202). Helical members 40, 45 are inflated simultaneously or alternately (steps 204, 206). Helical members 40, 45 are deflated (steps 208, 210), and catheter 10 is removed from the patient.

Figure 13:
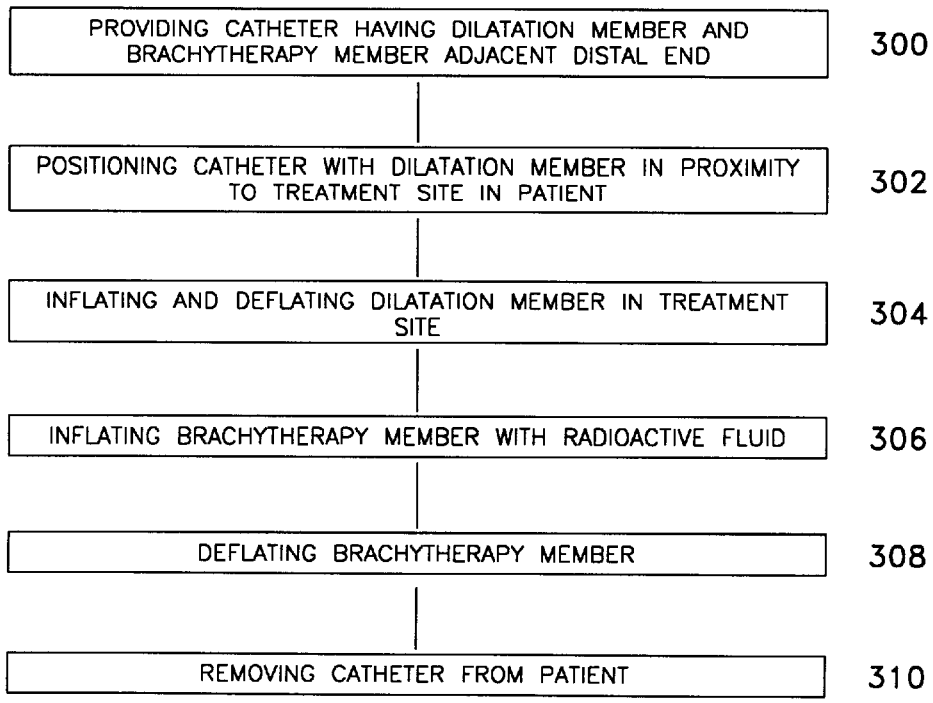
FIG. 13 is a flow chart depicting an alternative method of using a catheter in accordance with the present invention.

According to an alternative method of using an embodiment of the invention, as shown in FIG. 13, catheter 10 is percutaneously inserted into the patient's vessels, preferably traversing a vein or artery until helical treatment member 40 reaches the desired treatment site (steps 300, 302). Helical member 40 is inflated and deflated (step 304) according to usual procedures for PTCA. Then, helical member 45 is inflated with radioactive fluid (step 306), then deflated (step 308), and catheter 10 is removed from the patient (step 310).

In selecting the appropriate isotope to use in forming the radioactive material, typically in the form of an aqueous solution, several factors must be considered. For example, it is preferred that a low dose of radiation is delivered for a sufficient period of time to suppress the proliferative response to injury in vivo. Thus, total dose (generally measured in centi Gray) is typically determined by the specific activity of the radiation emitting material (generally measured in micro Curies ($\mu$Ci)) multiplied by time. However, the total dose must be balanced between the desired interruption of an injury response versus the detrimental mutagenic effect of tissue exposure to excessive radiation. Suitable radioactive materials include beta emitting isotopes (e.g., $Sr^{90}$, $Yt^{90}$, or $P^{32}$) or gamma emitting isotopes (e.g., an iridium isotope). Preferably, the solution contains a $\beta$-radiation emitting isotope. More preferably, the $\beta$-radiation emitting isotope has a half-life of about 150 days or less. Most preferably, the solution contains a sterile aqueous solution of $Sr^{90}$ or $Yt^{90}$.

The preceding specific embodiments are illustrative of the practice of the invention. Various modifications and alterations of this invention will become apparent to those skilled in the art without departing from the scope and spirit of this invention, and it should be understood that this invention is not to be unduly limited to illustrative embodiments set forth herein.

What is claimed is:

1. A catheter for treatment of a vessel in a patient, the catheter comprising:

an elongate catheter body having proximal and distal ends, first and second lumens extending therethrough, and a treatment portion disposed near the catheter body distal end; and first and second helical balloons extending through the treatment portion and being in fluid communication with the first and second lumens, respectively, the first and second helical balloons being arranged in parallel relationship to form first and second helical elements, respectively, of a double helix configuration, wherein the first helical balloon and the second helical balloon are adapted to be independently inflated into contact with the vessel.

2. A method of treating a narrowing in a vessel of patient, the method comprising the steps of:

providing a catheter comprising an elongate catheter body having proximal and distal ends, first and second lumens extending therethrough, and first and second independently inflatable helical members of a double helix configuration disposed adjacent the distal end;

positioning the catheter such that the double helix configuration is in proximity to the narrowing;

inflating the first helical member;

inflating the second helical member;

deflating the first helical member;

deflating the second helical member; and removing the catheter.

3. The method of claim 2 wherein the step of inflating the first helical member causes the first helical member to dilate die narrowing.

4. The method of claim 2 wherein the step of inflating the second helical member further comprises inflating the second helical member with radioactive fluid to irradiate the narrowing.

5. The method of claim 2 wherein the steps of inflating the first and second helical members are performed simultaneously.

6. A method of treating a narrowing in a vessel of a patient, the method comprising the steps of:

providing a catheter comprising an elongate catheter body having proximal and distal ends, first and second lumens extending therethrough, an inflatable dilatation member mounted about the catheter body near the distal end, and an inflatable brachytherapy member mounted about the catheter body near the distal end;

positioning the catheter such that the dilatation member is in proximity to the narrowing;

inflating and deflating the dilatation member to dilate the narrowing;

inflating the brachytherapy member with radioactive fluid to irradiate the narrowing;

deflating the brachytherapy member; and removing the catheter from the patient.

7. The method of claim 6 wherein the dilatation member is a tubular dilatation balloon mounted generally coaxially about the catheter.

8. The method of claim 6 wherein the dilatation member is a helical dilatation balloon mounted spirally about the catheter body.

9. The method of claim 8 wherein the brachytherapy member is a helical balloon mounted spirally about the catheter body such that the brachytherapy member and the dilatation member form independently inflatable helical members of a double helix configuration disposed adjacent the distal end.

10. The method of claim 9 wherein inflating only one of either the brachytherapy member or the dilatation member into contact with the narrowing forms a helical perfusion channel through the double helix configuration.

11. The method of claim 6 wherein the brachytherapy member is mounted adjacent the dilatation member, the method further comprising the step of positioning the catheter such that the brachytherapy member is in proximity to the narrowing.

* * * * *

UNITED STATES PATENT AND TRADEMARK OFFICE
CERTIFICATE OF CORRECTION

PATENT NO. : 6,679,860 B2
APPLICATION NO. : 09/885072
DATED : January 20, 2004
INVENTOR(S) : Mark L. Stiger It is certified that error appears in the above-identified patent and that said Letters Patent is hereby corrected as shown below:

Column 8, line 64, "of patient," should be changed to -- of a patient --

Column 9, line 13, "dilate die" should be changed to -- dilate the --

Signed and Sealed this

Second Day of January, 2007

JON W. DUDAS
*Director of the United States Patent and Trademark Office*